(12) United States Patent
Lazarof

(10) Patent No.: US 8,828,066 B2
(45) Date of Patent: Sep. 9, 2014

(54) SECURING MECHANISM WITH DUAL EXPANDABLE ENDS

(75) Inventor: Sargon Lazarof, Encino, CA (US)

(73) Assignee: Sargon Lazarof, Encino, CA (US)

( * ) Notice: Subject to any disclaimer, the term of this patent is extended or adjusted under 35 U.S.C. 154(b) by 1261 days.

(21) Appl. No.: 12/012,278

(22) Filed: Feb. 1, 2008

(65) Prior Publication Data

US 2008/0208264 A1    Aug. 28, 2008

Related U.S. Application Data

(60) Provisional application No. 60/899,245, filed on Feb. 1, 2007.

(51) Int. Cl.
    *A61B 17/56*    (2006.01)
(52) U.S. Cl.
    USPC .......................................................... 606/310
(58) Field of Classification Search
    USPC ........................... 606/300–331; 433/173–176
    See application file for complete search history.

(56) References Cited

U.S. PATENT DOCUMENTS

| | | | |
|---|---|---|---|
| 3,708,883 A * | 1/1973 | Flander | 433/174 |
| 5,004,421 A | 4/1991 | Lazarof | |
| 5,087,199 A * | 2/1992 | Lazarof | 433/173 |
| 5,489,210 A * | 2/1996 | Hanosh | 433/173 |
| 5,611,688 A | 3/1997 | Hanosh | |
| 5,931,674 A * | 8/1999 | Hanosh et al. | 433/173 |
| 6,142,782 A | 11/2000 | Lazarof | |
| 6,227,860 B1 * | 5/2001 | Hobo | 433/173 |
| 6,371,989 B1 * | 4/2002 | Chauvin et al. | 623/17.11 |
| 6,506,051 B2 * | 1/2003 | Levisman | 433/173 |
| 6,767,350 B1 * | 7/2004 | Lob | 606/63 |
| 6,991,461 B2 * | 1/2006 | Gittleman | 433/173 |
| 7,828,848 B2 * | 11/2010 | Chauvin et al. | 623/17.16 |
| 2003/0014054 A1 * | 1/2003 | Huebner | 606/73 |
| 2005/0042574 A1 | 2/2005 | Lazarof | |

* cited by examiner

*Primary Examiner* — Kevin T Truong
*Assistant Examiner* — Christopher Beccia

(57) ABSTRACT

The present invention relates generally to medical/dental devices for fixing bone fractures, anchoring of bones, or anchoring of prosthetics to bones. The device generally relates to molly bolts, expandable screws, or devices/screws with expansion or locking mechanisms. More particularly, the present invention concerns an implant assembly which includes a tubular body portion that can be positively secured within a bore in a bone or prosthetic by expander mechanism at both ends of the tubular body portion.

12 Claims, 4 Drawing Sheets

*Fig. 2*
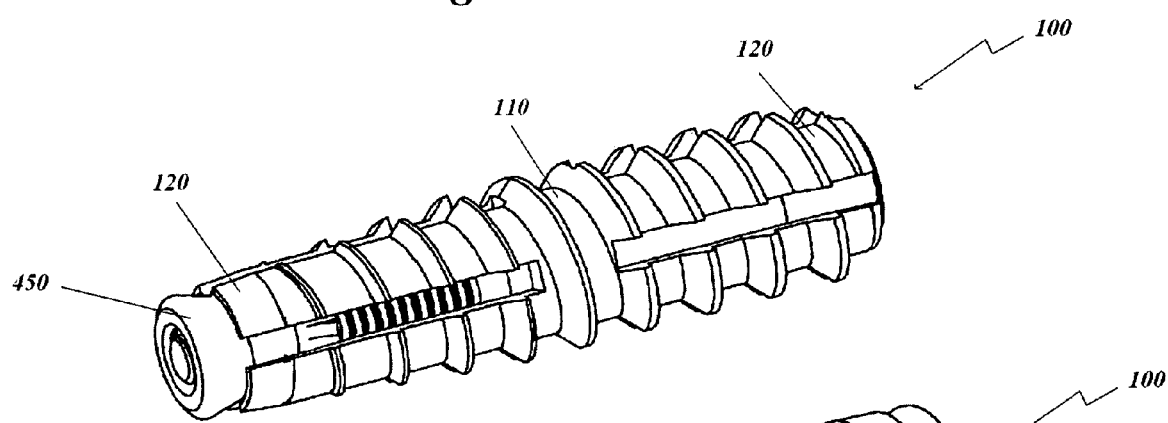
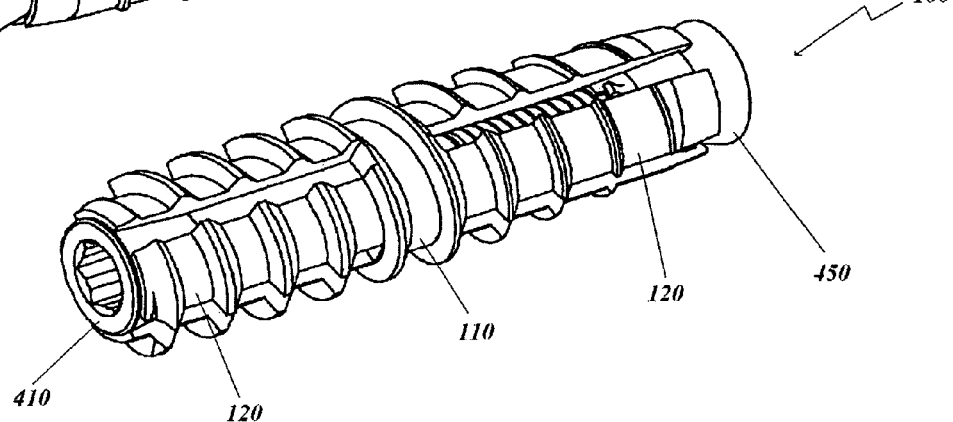
*Fig. 3*

SECURING MECHANISM WITH DUAL EXPANDABLE ENDS

CROSS-REFERENCE TO RELATED APPLICATIONS

The present invention claims priority to provisional application 60/899,245 filed on Feb. 1, 2007.

FEDERALLY SPONSORED RESEARCH

Not Applicable

SEQUENCE LISTING

Not Applicable

BACKGROUND OF THE INVENTION

The present invention relates generally to medical/dental devices for fixing bone fractures, anchoring of bones, or anchoring of prosthetics to bones. The device generally relates to molly bolts, expandable screws, or devices/screws with expansion or locking mechanisms. More particularly, the present invention concerns an implant assembly which includes a tubular body portion that can be positively secured within a bore in a bone or prosthetic by expander mechanism at both ends of the tubular body portion.

Use of mechanical locking means for securing bone fractures, anchoring of bones, or anchoring of prosthetic to bone are old in the art. Exemplary of such devices is the device described in U.S. Pat. No. 3,708,883 issued to Flander. An improved dental implant is illustrated and described in U.S. Pat. Nos. 5,004,421 and 5,807,199 issued to Lazarof. The Lazarof dental implant makes use of mechanical securement means. In one form, the Lazarof implant is positively secured within the bore in the bone by two separate but cooperating securement mechanisms. The first securement mechanism comprises self-tapping, external threads provided on the tubular body of the device which are threaded into the bone by rotating the device in a first direction. The second cooperating securement mechanism comprises a plurality of bone penetrating anchor blades formed on the skirt portion of the tubular body which are moved into a bone engagement position only after the implant has been secured into the bone. The anchor blades are moved into the bone engagement configuration by rotating a threaded expander member also in a first direction.

SUMMARY

The present invention relates to a device for securing two components together, namely, prosthetics-to-bone, or bone-to-bone, etc. The device comprises an elongated hollow body with expandable skirts at both ends of the elongated hollow body. The device further comprises a draw screw having a head captured within the hollow body that engages the internal of the hollow body. The device further comprises a threaded shank at the end of the draw screw head which extends to an end of one skirt. At the end of the threaded shank is an expansion nut for expanding the skirt at this end of the device.

FIGURES

FIGS. 1 through 3 shows the device of the present invention.

REFERENCE NUMBERS

Figure 1:
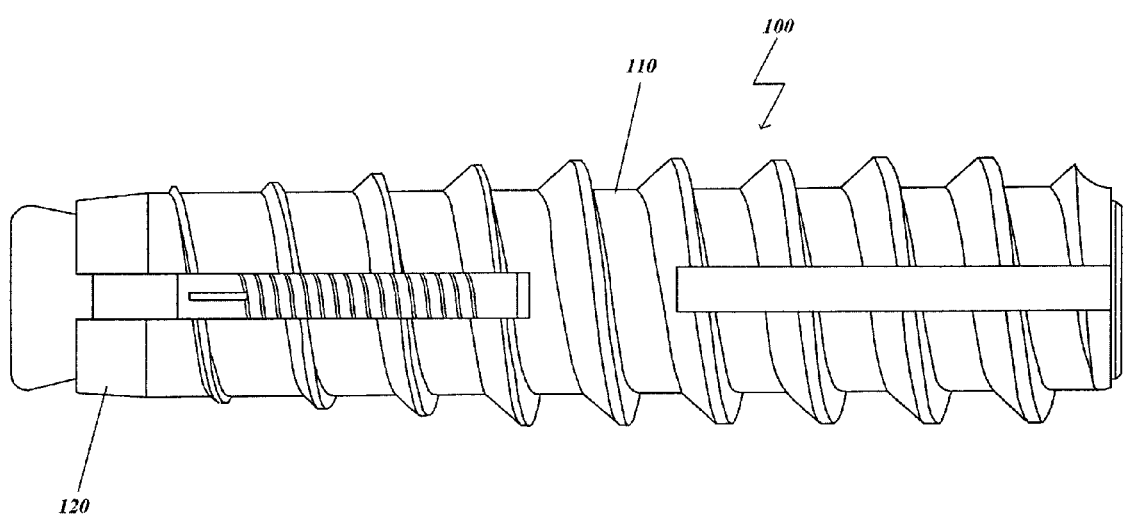
Figure 4:
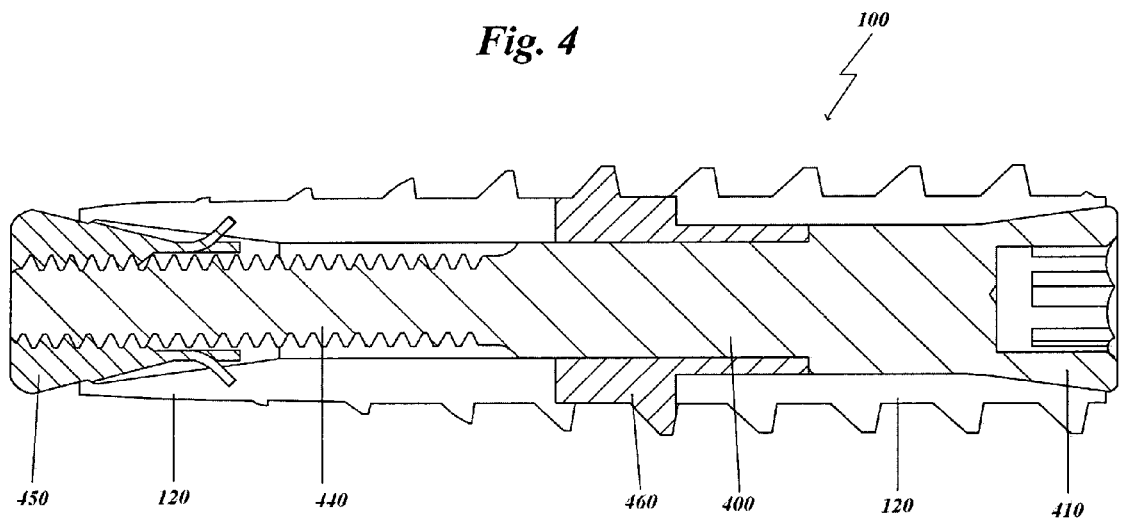
FIGS. 4 and 5 are cut out views of the device of the present invention.

100 . . . Securing Device
110 . . . Hollow Body
120 . . . Skirt
400 . . . Draw Screw
410 . . . Draw Screw Head
440 . . . Threaded Shank
450 . . . Expansion Nut
460 . . . Blocking Edge

DESCRIPTION

The present invention relates to a device for securing two components together, namely, prosthetics-to-bone, or bone-to-bone, etc. The device of the present invention is shown in FIGS. 1 through 4. FIGS. 1 through 4 discloses the device 100 of the present invention. The device 100 comprises an elongated hollow body 110 with expandable skirts 120 at both ends of the elongated hollow body 110. The device 100 further comprises a draw screw 400 having a head 410 captured within the hollow body 110 that engages the internal of the hollow body 110. The device 100 further comprises a threaded shank 440 at the end of the draw screw head 410 which extends to an end of one skirt 120.

At the end of the shank 440 of the draw screw 400 is an expansion nut 450 having a skirt-engaging side wall and an inner threaded cavity. Rotation of the draw screw 400 through the inner cavity of the expansion nut 450 causes radial movement of the skirts 120 from the first retracted position to the second expanded position. The expansion nut 450 may be eliminated if expansion of the skirts 120 at the end farthest away from the head 410 is not desired.

The head 410 of the draw screw 400 is flared, whereby rotation of the draw screw 400 through the inner cavity of the hollow body chamber 220 causes radial movement of the skirt 120 from the first retracted position to the second expanded position. The interior of the elongated hollow body 110 further comprises a blocking edge 460 for stopping the movement of the expansion nut 450. While the head 410 of the draw screw 400 may be flared, in an alternative form, the head can be unflared such that rotation of the draw screw 400 in the expansion direction will not cause the skirt 120 closes to the head 410 to expand.

To further aid in the expansion, skirt 120 may include an inclined internal surface. The skirt-engaging side wall of the expansion nut 450 may also have an inclined external surface moveable into engagement with the inclined internal surface of the skirt 120 upon rotation of the draw screw 400 through the inner cavity of the expansion nut 450. The skirt 120 may also be split such that at least two anchor segments movable from the first retracted position to the second expanded position is created. The split in the skirt may be a plurality of circumferentially spaced, longitudinally extending slits which separate the anchor segments.

The exterior of the elongated hollow body chamber 220 may be threaded such that selected components may be threadably connected. The threading prevents the device 100 from sliding out of the connection points created in the components to be connected.

To use the device 100 of the present invention two holes are created, one in each of the two components to be connected. The holes should be the same size or slightly larger than the outer diameter of the device 100. Ideally, the end with the expansion nut 450 would be placed into the first hole. The draw screw 400 is rotated such that the expansion nut 450 travels up the threaded shank 440. As the expansion nut 450 travels up the threaded shank 440, the skirt 120 is pushed out and expands to secure to the first component.

The second component to be attached to the first component is then inserted such that the protruding end of the device 100 passes into the hole in the second component. The hole in the second component may be drilled through so that the draw screw head 410 is accessible. Since the expansion nut 450 is blocked from further movement by the blocking edge 460, continued rotation of the draw screw 400 causes the draw screw 400 to move towards the center of the device 100. As the draw screw 400 moves towards the center of the device 100, the flanged head on the draw screw 400 causes the skirt 120 closes to the draw screw head 410 end to expand. The expansion of the skirt 120 secures the device 100 to the second component which in turns connects the first component to the second component.

Alternatively, instead of having a hole that provides access to the draw screw head 410, the draw screw head 410 may be magnetic. A head 410 with magnetic characteristics allows the draw screw 400 to be rotated with a magnetized screw or drill. As the draw screw is rotated, the skirt 120 expands to secure the device 100 to the second component which in turns connects the first component to the second component.

Figure 5:
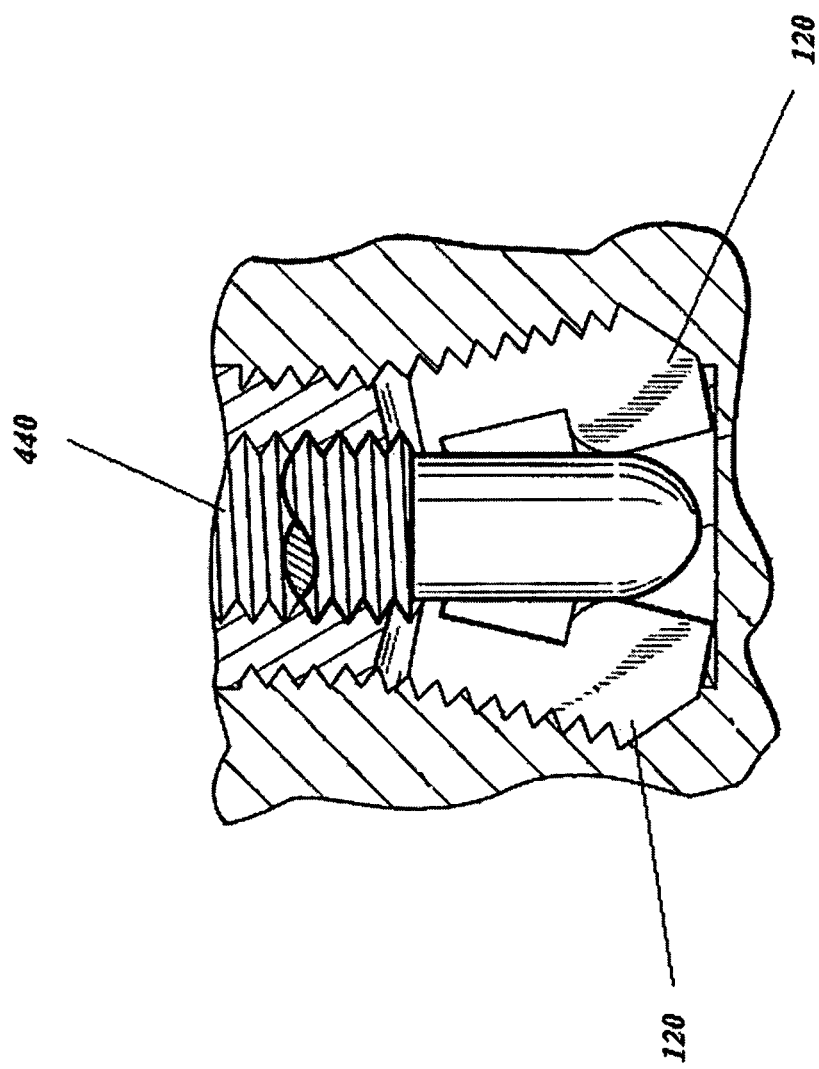

In an alternative of the device 100 of the present invention as shown in FIG. 5, the interior of the skirts 120 farthest away from the draw screw head 410 is enlarged such that the passageway from the hollow body 110 through the skirts 120 are narrowed or closed completely. The initial starting position of the threaded shank 440 would be within the hollow body 110 and may be just beyond the enlarged section of the skirts 120. All other aspects of the device 100 may be similar to those discussed above.

In another embodiment of the device 100 in this alternative form, the flare on the head 410 may be eliminated such that the skirts 120 closest to the head 410 is not expanded.

In another embodiment of the device 100 in this alternative form, the enlargement of the interior of the skirts 120 is removed such that the skirts 120 at the end farthest from the head is not expanded when the draw screw 400 is rotated into the expanded position.

To use the device 100 of the present invention in this alternative form, the device 100 is inserted into prepared holes in objects to be connected. As the draw screw 400 is rotated in the proper direction for expansion, both the skirts 120 farthest away from the draw screw head 410 and the skirts 120 closest to the draw screw head 410 are forced to expand due to the pushing of the farthest skirts 120 by the threaded shank 440 and the draw screw head 410 on the closest skirts 120, respectively. The expansion of both skirts 120 causes a tight connection between the components to be joined.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

While specific systems and methods have been disclosed in the preceding description, it should be understood that these specifics have been given for the purpose of disclosing the principles of the present invention and that many variations thereof will become apparent to those who are versed in the art.

What is claimed is:

1. An dual end expandable implant attachment assembly, comprising:

A one-piece elongated hollow body with expandable skirts at both ends of the elongated hollow body;

A draw screw having a head captured within a proximal end of the hollow body and a threaded shank connected to the head and which extends to a distal end of the hollow body;

The head of the draw screw is flared, whereby rotation of the draw screw through the inner cavity of the hollow body causes radial movement of the expandable skirts at the proximal end of the hollow body from the first retracted position to the second expanded position; and At the end of the threaded shank of the draw screw, located partially inside the distal end of the hollow body, is a flared expansion nut having a skirt-engaging side wall and an inner threaded cavity into which the shank of the draw screw is threaded, whereby rotation of the draw screw through the inner cavity of the expansion nut causes the expansion nut to move furtherinside the distal end of the elongated hollow body forcing radial movement of the expandable skirts at the distal end of the hollow body from the first retracted position to the second expanded position.

2. The assembly of claim 1, wherein the interior of the elongated hollow body comprises a blocking edge for stopping the movement of the expansion nut.

3. The assembly of claim 1, wherein the skirt includes an inclined internal surface, and wherein the skirt-engaging side wall of the expansion nut has an inclined external surface moveable into engagement with the inclined internal surface of the skirt upon rotation of the draw screw through the inner cavity of the expansion nut.

4. The assembly of claim 1, wherein the skirts comprises at least two anchor segments movable from the first retracted position to the second expanded position.

5. The assembly of claim 1, wherein the exterior of the elongated hollow body is threaded such that a selected component can be threadably connected to the assembly.

6. The assembly of claim 4, wherein the skirt includes a plurality of circumferentially spaced, longitudinally extending slits which separate the anchor segments.

7. The assembly of claim 1, wherein the draw screw head has magnetic characteristics.

8. An dual end expandable implant attachment assembly, comprising:

A single-piece elongated hollow body with expandable skirts at both ends of the elongated hollow body;

A draw screw having a head captured within a proximal end of the hollow body and a threaded shank connected to the head and which extends to a distal end of the hollow body;

The head of the draw screw is flared, whereby rotation of the draw screw through the inner cavity of the hollow body causes radial movement of the explandable skirt at the proximal end of the hollow body from the first retracted position to the second expanded position; and An interior of the expandable skirts at the distal end of the hollow body is enlarged so that passageway at the distal end of the hollow body is narrower than the passageway through the remainder of the hollow body such that when draw screw is rotated, the threaded shank passes through the narrower passageway causing the distal end of the hollow body to move from the first retracted position to the second expanded position.

9. The assembly of claim 8, wherein the skirts comprises at least two anchor segments movable from the first retracted position to the second expanded position.

10. The assembly of claim 8, wherein the exterior of the elongated hollow body is threaded such that a selected component can be threadably connected to the assembly.

11. The assembly of claim 9, wherein the skirt includes a plurality of circumferentially spaced, longitudinally extending slits which separate the anchor segments.

12. The assembly of claim 8, wherein the draw screw head has magnetic characteristics.

\* \* \* \* \*